US00PP16727P3

(12) United States Plant Patent
Sanguthai

(10) Patent No.: US PP16,727 P3
(45) Date of Patent: Jun. 27, 2006

(54) ***DENDROBIUM* PLANT NAMED 'WHITE ANNA'**

(50) Latin Name: *Dendrobium hybrid*
Varietal Denomination: White Anna

(76) Inventor: Surapon Sanguthai, 42 Moo 6, Budthamonthol 4th Rd., Sampran, Nakhonphatom (TH), 73220

( * ) Notice: Subject to any disclaimer, the term of this patent is extended or adjusted under 35 U.S.C. 154(b) by 86 days.

(21) Appl. No.: 10/769,689

(22) Filed: Jan. 26, 2004

(65) Prior Publication Data

US 2005/0166296 P1 Jul. 28, 2005

(51) Int. Cl.
*A01H 5/00* (2006.01)

(52) U.S. Cl. ..... Plt./311

(58) Field of Classification Search ..... Plt./311
See application file for complete search history.

*Primary Examiner*—Anne Marie Grunberg
*Assistant Examiner*—June Hwu

(57) ABSTRACT

A new and distinct cultivar of *Dendrobium* named 'White Anna' characterized by long lasting, round-shape white flowers on a long inflorescence.

4 Drawing Sheets

BACKGROUND OF THE INVENTION

The present invention is directed to a new and distinct cultivar of *Dendrobium*, botanically know as *Dendrobium* hybrid, and having the cultivar name 'White Anna'.

The new cultivar was an elite somaclonal variant of *Dendrobium* hybrid 'Anna Bride' (*Dendrobium* Ekapol 'Anna'×*Dendrobium* Shavin White '5N') selected, from approximately 10,000 micropropagated plants of the original cultivar grown for cut-flower production, by the inventor.

Asexual propagation of the new cultivar in Nonthaburi, Thailand by division and micropropagation has demonstrated the uniformity and stability througout successive generations of this new *Dendrobium*.

SUMMARY OF THE INVENTION

The following traits have been repeatedly recorded in the new cultivar grown under 50% shade condition of a commercial cut flower nursery in Nonthaburi, Thailand with common horticultural practice.

The features that in combination are believed to distinguish 'White Anna' from other known cultivars of *Dendrobium* include : color of petals, sepals and labellum; round-shape flowers; long postharvest life; long inflorescence.

Plants of the new *Dendrobium* can be compared to plants of its original cultivar, the *Dendrobium* hybrid 'Anna Bride' (U.S. Plant patent application Ser. No. 10/769,688) Plants of the new *Dendrobium* differ from plants of the cultivar 'Anna Bride' which is the most resemblance, in the following characteristics 1. The flower of the new *Dendrobium* is white, instead of light purplish pink with white center as found in 'Anna Bride'.

The new cultivar has white petals, sepals and labellum whilst its female parent, *D.* Ekapol 'Anna', has pink petals, sepals and labellum. On the other hand, the flowers of the new cultivar has broader petals and rounder shape than its male parent, *D.* Shavin White '5N'.

BRIEF DESCRIPTION OF ILLUSTRATIONS

The accompanying color photographs illustrate the overall appearance of the new cultivar as true in color as possible in color illustration of this type.

DESCRIPTION OF THE NEW VARIETY

Figure 1:
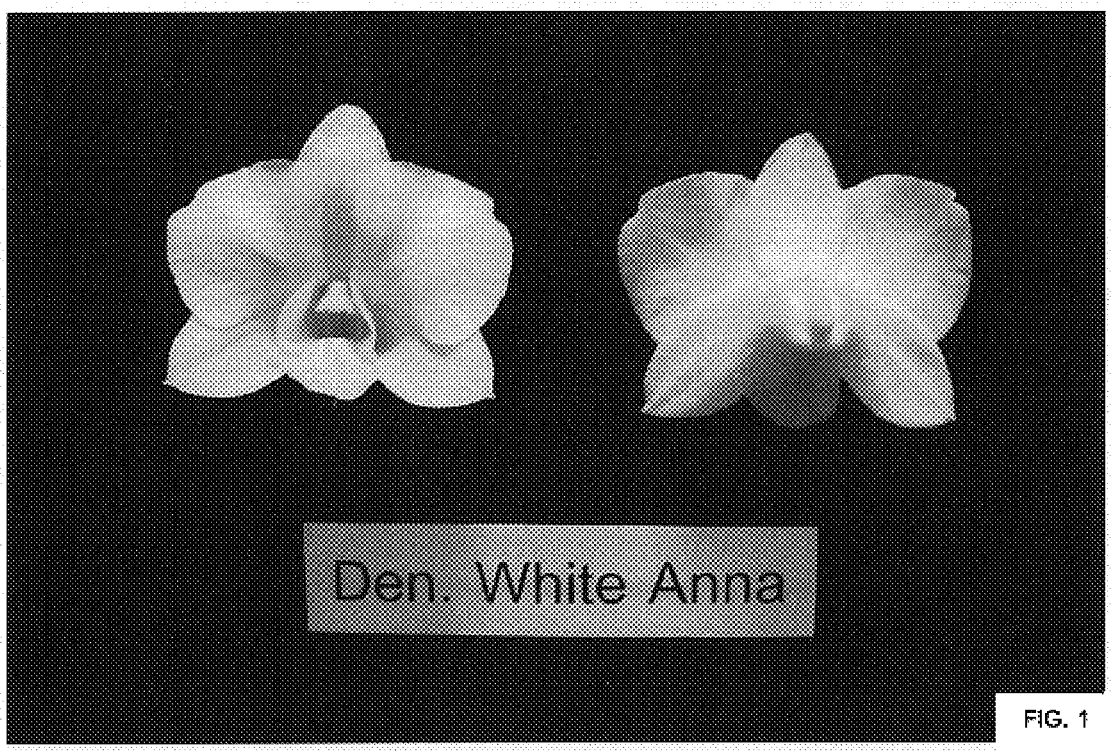
FIG. 1 is a front and rear view of *Dendrobium* hybrid 'White Anna'.
Figure 2:
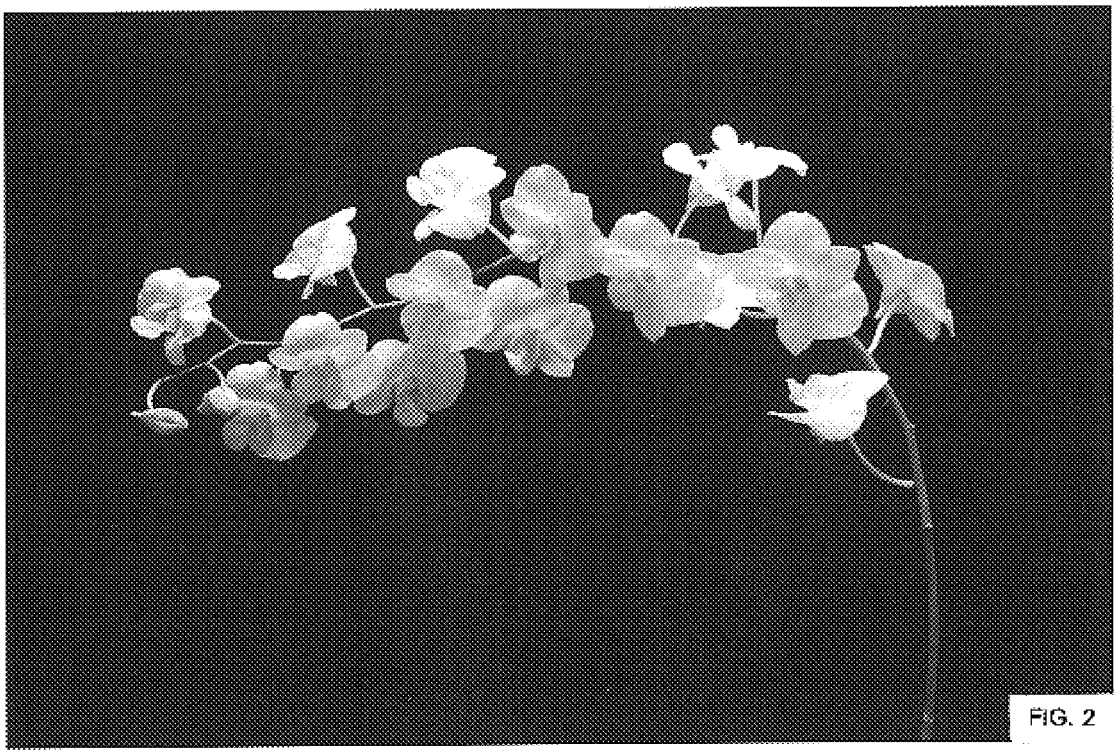
FIG. 2 is an inflorescence of *Dendrobium* hybrid 'White Anna'.
Figure 3:
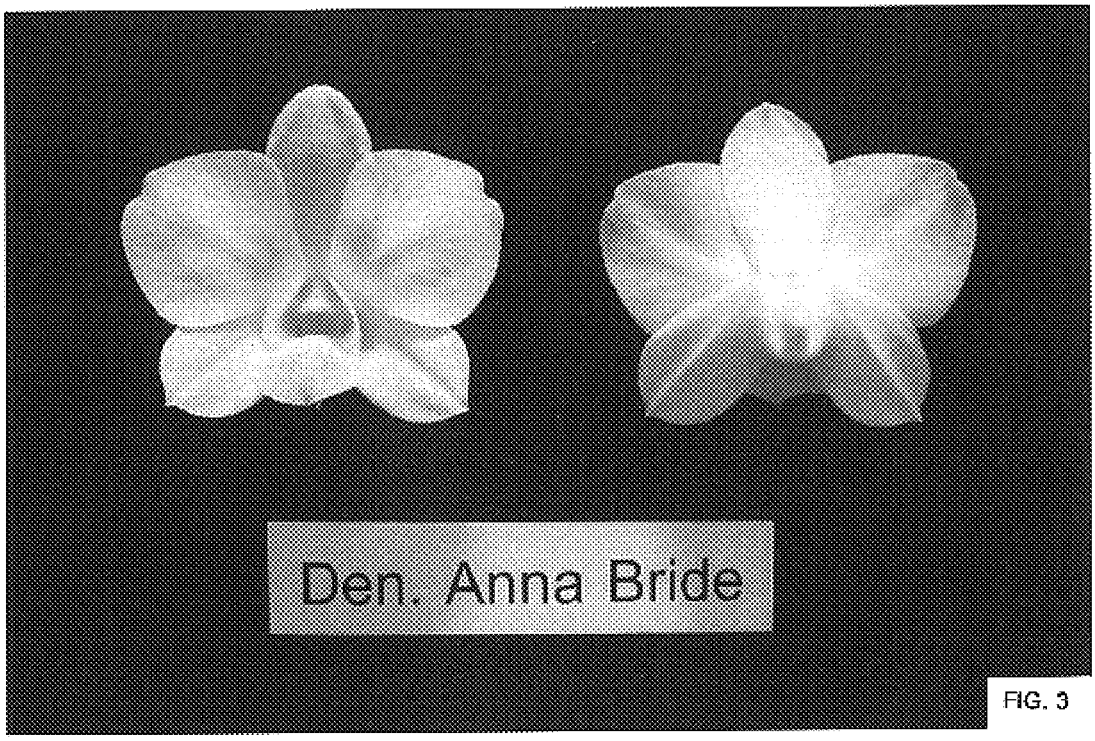
FIG. 3 is a front view of *Dendrobium* hybrid 'Anna Bride'.
Figure 4:
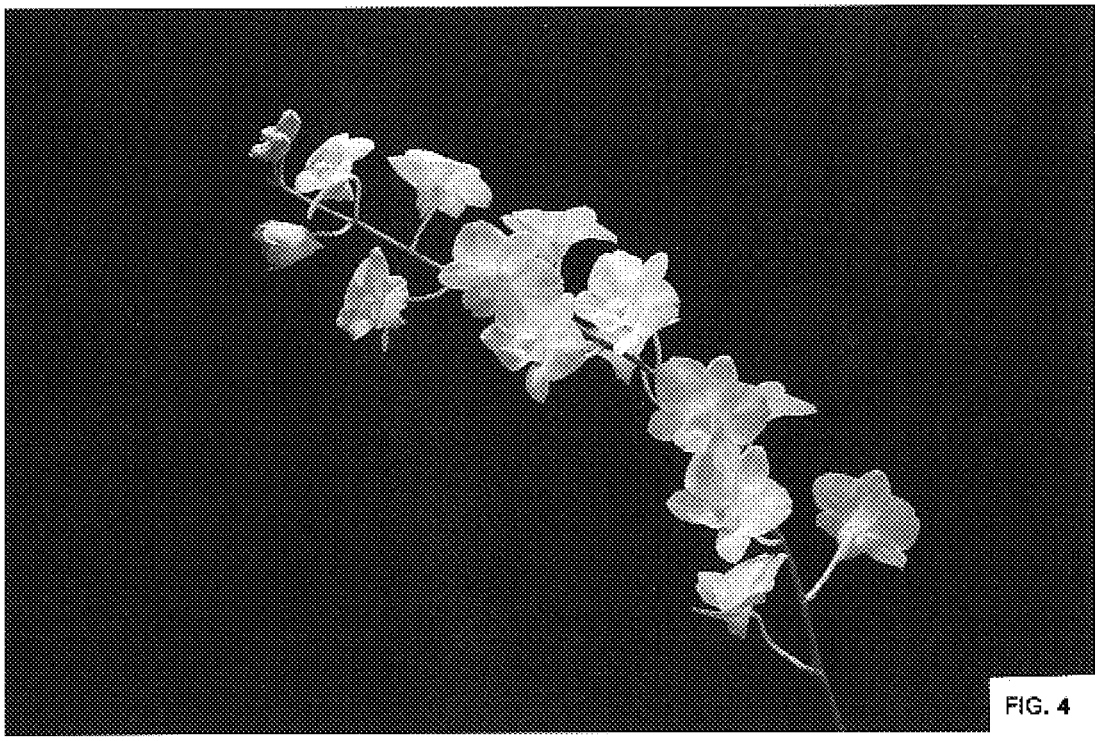
FIG. 4 is an inflorescence of *Dendrobium* hybrid 'Anna Bride'.

The following observations were made of 3-year old plants of the new variety grown under light shade conditions, in Nonthaburi, Thailand during the months of March through August. Phenotypic expression may vary with environmental, cultural and climatic conditions, as well as differences in conditions of light and medium.

Throughout this specification, color references and/or values are based upon The Royal Horticultural Society Colour Chart (2001 edition) and terminology used in the color descriptions herein refers to plate number in this color chart except where common terms of color definition are employed.

Original cultivar: *Dendrobium* hybrid 'Anna Bride'.
Propagation: By division and micropropagation.
Plant:

*Shape.*—Pseudobulb, cylidrical and upright.

*Size.*—Pseudobulb about 50–70 cm high; diameter about 2.0–2.5 cm at the age of 2.5–3.0 years.

*Color.*—Pseudobulb near 143 C.

*Growth habit.*—Resulting from branching of rhizome, the new pseudobulb emerges close to the old pseudobulb.

Foliage:

*Leaf shape.*—Lanceolate with an acute apex, an obtuse base and entire margin.

*Size.*—Length about 15–20 cm, width about 4.0–5.0 cm.

*Surface.*—Smooth; upper near 141 A; lower near 143 B.

*Aspect.*—Distichous alternate array on pseudobulb.

*Leaf sheath.*—Length about 15–20 cm; near 143 B.

Inflorescence: From apical and $3^{rd}$ to $4^{th}$ axillary buds of pseudobulb; 16 to 23 flowers.

*Raceme.*—Erect, near 144A.

*Pedunole.*—Length about 15–18 cm; diameter about 0.35 cm; near 144A.

*Rachis.*—Length about 40–45 cm; diameter about 0.45 cm; near 144A.

*Flower.*—Natural spread about 6.5–7.2 cm; vertical length about 5.3–5.8 cm; dorsal sepal about 1.8 to 2.0 cm wide, 3.7 to 3.9 cm long, near N 155 C, abaxil near 155 C, elliptic with cuspidate tip, entire; lateral sepals about 1.8 to 2.0 cm wide, 4.5 to 4.7 cm long, near N 155 C, abaxil near oblong with cuspidate tip, entire; petals about 3.4 to 3.5 cm wide, 3.7 to 3.9 cm long, near N 155 C, abaxil near 155 C, rhombic with acute tip, entire; labellum about 1.8 to 2.0 cm wide, 4.2 to 4.3 cm long, near 155 C, non-pubescence, trilobed rhombic, no appendage, labellar gill 5 rows, near 149 D, abaxil near 155 C; column about 0.63 cm long, diameter about 0.45 cm, near 150 C; spur about 1.8 cm long, near 157 D; pollinia 2 in number, about 0.1 cm wide and 0.2 cm long, near 7A; pedicel about 4.8–4.9 cm long, diameter 0.25 cm, near 145 D; nearly open bud about 1.5 cm wide, about 3.5 cm long, near 149 C.

*Vase life.*—About 12–15 days in water.

*Disease and pest resistance.*—None observed.

Plant of the *Dendrobium* 'White Anna' is upright and clumping. The inflorescence is long with 16–23 flowers, long lasting. Flower is white with light yellowish green gills. Petals overlap sepals.

I claim:

1. A new and distinct *Dendrobium* named 'plant White Anna'substantially as illustrated and described.

* * * * *